United States Patent [19]

Anthony

[11] Patent Number: 5,350,562
[45] Date of Patent: Sep. 27, 1994

[54] METHOD AND APPARATUS FOR STERILIZATION AND SEPARATION OF PLASTIC AND NON-PLASTIC MEDICAL WASTES

[76] Inventor: Frank H. Anthony, 326 Atherton Dr., Metaire, La. 70005

[21] Appl. No.: 43,649

[22] Filed: Apr. 6, 1993

Related U.S. Application Data

[63] Continuation-in-part of Ser. No. 682,069, Apr. 9, 1991, Pat. No. 5,256,861.

[51] Int. Cl.⁵ .................. A61L 2/04; A61L 11/00; B03B 1/02; B29B 17/02
[52] U.S. Cl. .................. 422/1; 422/307; 209/11; 241/65; 241/99; 241/DIG. 38; 264/37; 423/DIG. 18
[58] Field of Search .................. 432/261; 209/11; 264/37; 241/23, 25, 37.5, 65, 68, DIG. 38, 99; 422/1, 307, 22; 521/40; 29/403.3, 403.4; 423/DIG. 18

[56] References Cited

U.S. PATENT DOCUMENTS

| | | | |
|---|---|---|---|
| 3,599,788 | 8/1971 | Fyle et al. | 209/11 |
| 3,958,936 | 5/1976 | Knight, Jr. | 422/1 X |
| 4,552,728 | 11/1985 | Taylor | 422/307 X |
| 4,629,411 | 12/1986 | Bücheler | 264/37 X |
| 4,860,958 | 8/1989 | Yerman | 264/37 X |
| 4,992,217 | 2/1991 | Spinello | 422/307 X |
| 5,003,892 | 4/1991 | Bricken | 422/1 X |
| 5,061,735 | 10/1991 | Zielinski | 209/11 X |
| 5,124,126 | 6/1992 | Ripp | 422/1 X |
| 5,213,758 | 5/1993 | Kawashima | 422/307 X |
| 5,225,130 | 7/1993 | Deiringer | 264/37 X |

*Primary Examiner*—Robert J. Warden
*Assistant Examiner*—E. Leigh Dawson
*Attorney, Agent, or Firm*—Nixon & Vanderhye

[57] ABSTRACT

Medical waste products including plastic and non-plastic elements are placed in a metal container which includes a raised insert element for supporting the waste above the bottom of the container. The container and used medical waste products are subjected to dry heat treatment at temperatures below the waste material flash points but of sufficient temperature and for a sufficient time to melt the plastic elements as well as to sterilize the contents. During the heating process the metal, rubber and other non-plastic elements remain on the raised insert; whereas, the molten plastic flows through or over the side of the insert to the bottom of the container. Upon cooling the plastic and non-plastic components of the medical waste products are separated as well as being sterile such that the container can be opened and the contents separately handled for appropriate recycling. The dry heat generator conveniently may be placed in a medical office or the like and is microprocessor controlled to obtain the desired end products. The processor additionally controls an electrical interlock system whereby the heat generator unit may not be opened until an entire heat cycle has been completed, and the waste products have cooled to a safe temperature.

18 Claims, 4 Drawing Sheets

FIG. 1
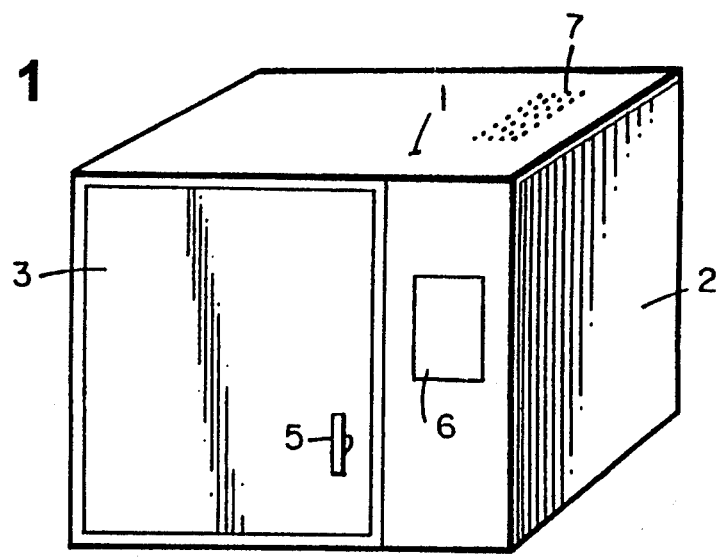
FIG. 2
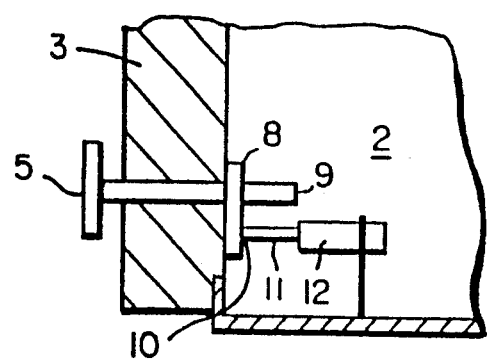
FIG. 2A
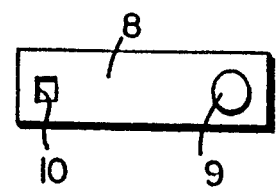
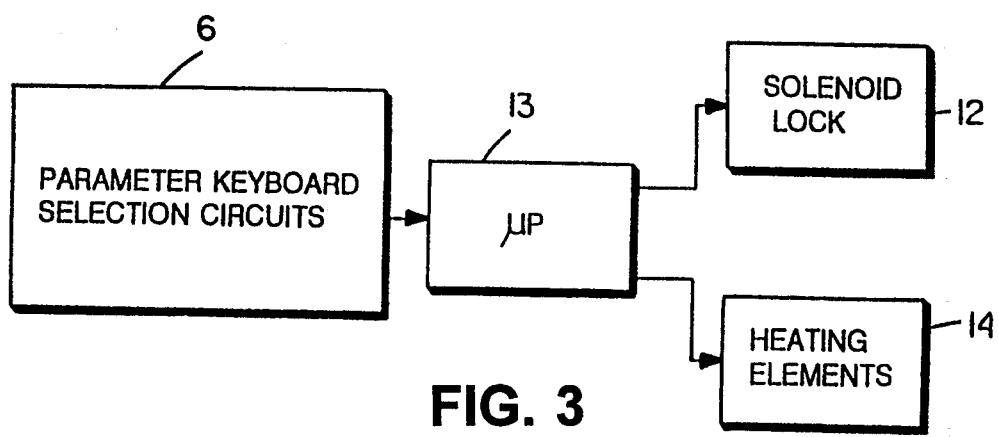
FIG. 3

METHOD AND APPARATUS FOR STERILIZATION AND SEPARATION OF PLASTIC AND NON-PLASTIC MEDICAL WASTES

This is a continuation-in-part of application Ser. No. 07/682,069, filed Apr. 9, 1991, now U.S. Pat. No. 5,256,861, issued on Oct. 26, 1993.

FIELD OF THE INVENTION

The invention relates to a method and apparatus for treating medical waste to obtain sterilization and separation of plastic and non-plastic components at relatively low temperatures that are below the flash points of the waste products.

BACKGROUND AND SUMMARY OF THE INVENTION

As is well known, satisfactory disposal methods associated with waste products present formidable problems to industry, governmental agencies and the like. However, the degree of difficulty in dealing with certain waste products such as medical waste is even more difficult in light of the potentially infectious nature of biomedical waste products, such as used syringes, intravenous tubing, petri dishes and the like. Such waste products may be made of all plastic elements or may include a mix of plastic, rubber and metal components.

Recognized methods of treating medical wastes include incineration, encapsulation or some other manner of rendering the contaminated waste products safe and unusable. Incineration, however, leads to still further problems, such as air pollution, and still further regulations pertaining to the elimination of metallic compounds from the exhaust fumes. For example, it is known that the red disposal bags presently used for medical waste include significant amounts of cadmium. For incineration, additional measures would be required to prevent the exhaust of such cadmium compounds and other hazardous constituents by way of incinerator exhausts.

Encapsulation in the disposal of medical sharps is also permissible in accordance with some regulations. For example, dentists in some localities may dispose of their medical sharps by encapsulating such waste in plaster. Clearly such treatment and handling processes, although authorized, present problems of convenience and practicality and do not eliminate or discourage the problem of illegal dumping.

Still further, in addition to sterilization of such waste products, it is environmentally desirable to recycle many of the materials included in the waste products. Thus, it is desirable to not only render the products safe but also in a condition such that the several materials are separated and readily recycled.

The principal object of my invention is that of treating medical waste products including plastic materials so as to render them harmless the same day of use and at any selected location, such as a doctor's office, thus eliminating any transportation and, therefore, the possibility of dumping untreated potentially infectious biomedical waste.

It is a still further object of the disclosed exemplary embodiments to separate the several materials included in medical wastes while simultaneously sterilizing the involved materials.

I have discovered that such objects can be obtained through the use of a container for the products and a dry heat generator that is useful in rendering medical waste products, such as syringes, tubing and various other wastes including plastic elements, harmless by subjecting such items and the container to a heat treatment. The temperature during treatment is sufficiently high to sterilize the various materials, as well as to melt the plastic bodies or elements within the container. Additionally, the container is constructed to include a raised portion or platform for collecting metal needles, rubber plungers, and the like, while allowing the molten plastic to pass through or over the raised portion so as to sink to the bottom of the container to form a liquid plastic pool separated from the other materials.

Since the melting temperatures of such plastic materials are substantially below their flash points, the heating function may be controlled both as to time and temperature such that a heating cycle will meet all government regulations pertaining to sterilization of both plastic and non-plastic materials but without any burning or incineration of the waste products. Moreover, the separated non-plastic elements remain on the raised portion of the container and, therefore, can be subsequently recycled as separate materials.

It is a further object of this invention to employ a reusable container constructed, for example, of stainless steel or other metal and including a raised interior portion of wire grating or screen with openings of a size so as to allow the molten plastic to pass through the grating to the bottom of the container. Alternatively, the raised portion may be a continuous metal plate with outer dimensions slightly smaller than the interior dimensions of the container to allow the molten plastic to pass along the sides of the plate to the container bottom.

Such containers may be of various sizes as determined by the nature of the waste products. Moreover, the containers may be used for holding the medical waste product until the container is either full or otherwise ready for sterilization and material separation. When placed in the dry heat generator and subjected to a heating cycle, the container with optional closure elements remain intact. However, the molten plastic materials will flow over or through the raised platform insert of the container to the bottom leaving the separated non-plastic material elements on the interior raised portion of the container. Upon cooling, the top of the container can be removed and the sterilized contents can be separately recycled in accordance with the type of separated materials.

It is a still further object of my invention to equip the dry heat generator with a safety lock feature whereby the door of the generator cannot be opened until an entire heat cycle has been completed, and the temperature of the waste products have been reduced to a predetermined safe temperature. The principal object of the safety lock system feature is that of preventing contact with medical wastes that have not been completely treated due to a loss of power, as well as preventing contact with treated sharps prior to cool down to a safe temperature.

A still further object of the invention is to include a high temperature afterburner at an exit port of the dry heat generator, as well as a charcoal filter for treating the fumes including metallic vapors, in such a manner as to eliminate any metallic or particle exhaust contents, as well as removing odors that might be generated in the process.

These and other objects and advantages of the present invention will become more apparent upon reference to the following specification, appended claims and drawings.

BRIEF DESCRIPTION OF THE DRAWINGS

FIG. 1 is a perspective view of an exemplary embodiment of my dry heat generator or autoclave useful in rendering medical waste safe for disposal and/or recycling;

FIG. 2 is a partial view of the side wall and door of the dry heat generator broken away to illustrate the mechanical and electrically operated lock mechanisms for preventing the opening of the door under potentially hazardous conditions;

FIG. 2A illustrates a side view of an exemplary mechanical latching member associated with the door handle of the dry heat generator;

FIG. 3 illustrates in block diagram form a microprocessor included in the dry heat generator for controlling the electrically operated solenoid door lock and heating elements of the dry heat generator and afterburner heating elements in response to input control information entered by way of pushbuttons or keyboard selection;

DETAILED DESCRIPTION OF THE DRAWINGS

Figure 4:
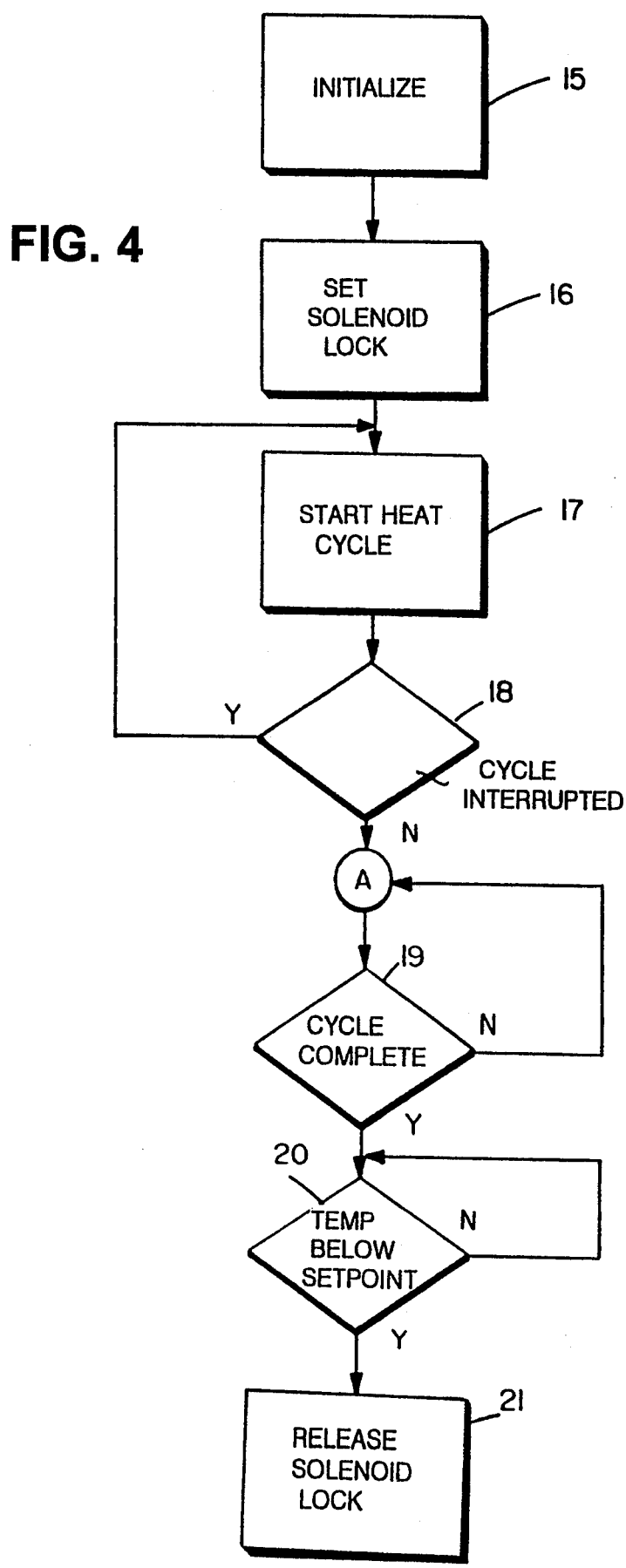
FIG. 4 is a flowchart of the operative steps followed by the microprocessor in the performance of a heating cycle in response to control signals from the input selection circuitry.

Safe disposal of medical waste products have presented formidable problems for some time. Certain of these products, including sharps, such as hypodermic syringes and the like, are particularly troublesome due to the potentially infectious nature of used hypodermic needles in combination with the likelihood of accidental punctures suffered by medical personnel in the handling of such medical sharps. In light of such problems, governmental agencies have enacted laws dictating the requirements and manner of disposing of such waste. One exemplary law pertaining to the treatment of sharps requires that such waste shall be treated by incineration, encapsulation or other means by which they are rendered unrecognizable as potentially infectious biomedical waste and otherwise rendered unusable.

Incineration or conventional encapsulation methods, however, are not practical or inherently produce additional problems such as air pollution, thus requiring still further legislative action dictating environmental safeguards. Moreover, disposal by conventional encapsulation or incineration methods usually involves repeated handling by various personnel increasing the chance of accidental punctures, as well as generating additional expense which in turn increases the likelihood of unlawful dumping or disposal.

I have discovered that medical waste including sharps principally comprising hypodermic syringes and intravenous needles having plastic bodies or tubing (such as polypropylene) along with the metal needles and rubber stoppers may be safely rendered unrecognizable, sterilized and separated as to plastic and non-plastic materials by way of my dry heat autoclave method. Moreover, the method is also applicable to other medical waste having plastic ingredients such as catheters, petri dishes, tubing and the like.

Such method involves no flame or other heat source which would provide sufficient heat to cause any of the involved materials to reach their flash points. The flash point of the plastic materials involved is approximately 730°, for example; whereas, the melting temperature for plastic syringe material is about 320° F. Accordingly, heating such medical waste in a suitable container at or above the melting point of the plastic material for a sufficient period of time will render the plastic and non-plastic materials sterile at a temperature well below the flash point of the materials, as well as separating the plastic and non-plastic waste materials for subsequent recycling.

FIG. 1 is a perspective view of an exemplary embodiment of my dry heat generator 1 which can be sized to conveniently fit on a shelf or desk in a doctor's office, for example. The dry heat generator or autoclave includes a cabinet 2 which may be loaded from the front by way of a hinged door 3, which includes a turnable handle 5 for operating a mechanical latch mechanism. The exemplary dry heat generator additionally includes a row of push buttons or a keyboard selection circuit 6 for selecting cycle parameters, such as temperature and time, as well as other control inputs such as start, set electrical latch, cycle reset and the like.

Additionally included in the interior of the cabinet of the heat generator unit 1 is an afterburner and filter unit connected to the heating chamber of unit 1 by way of an exit port (not shown) and exhausting through the cabinet 2 at vent openings 7. The afterburner unit may be of the nature disclosed in my U.S. Pat. No. 4,897,528 issued on Jan. 30, 1990, which includes a relatively high temperature heating element and condensing path. As described in the cited patent, the afterburner unit may additionally include a filtering unit such as an activated charcoal filter whereby the exhaust fumes passing through the unit and exiting through vents 7 are acted upon in such a manner as to eliminate any metallic or particulate matter, as well as removing odors that might be generated in the heating process.

As may be seen from a consideration of FIGS. 2 and 2A, handle 5 may be rotated to operate a mechanical latching element, such as 8, by way of shaft 9. Latching element 8 additionally includes an opening 10 for receiving the spring-loaded plunger 11 of solenoid 12. As will be subsequently explained, solenoid 12 and element 11 cooperate with the mechanical latching element 8 so as to form an electrically operated safety lock feature whereby the door 3 of unit 2 cannot be opened until an entire heat cycle has been completed, and the temperature of the waste products in the heating chamber of the unit 2 has been reduced to a predetermined safe temperature. As illustrated, the mechanical and electrical latching mechanisms are included in the side wall of unit 2. Moreover, as will be recognized by the artisan, the mechanical latching mechanism may take various forms including those with keyed or coded locking mechanisms. Provision must be made, however, for the inclusion of an electrical interlock feature of the aforementioned nature.

Additionally included in the insulated walls of the dry heat generator unit 2 is a microprocessor 13, which, as generally illustrated in FIG. 3, receives control inputs from selection circuitry associated with keyboard 6, as well as producing control outputs for operating an electrically operated interlock such as the solenoid 12 and controlling the operation of the heating elements 14 contained within unit 2 as well as in the afterburner.

Microprocessor 13 may be of conventional construction and include nonvolatile memory units such as a random access memory (RAM) for storing input information such as temperature and timing cycle set points, as well as elapsed time data and cycle interrupt flag data. The processor would additionally include a conventional read-only memory (ROM) for storing instructions for implementing the control process illustrated in FIG. 4 in flowchart format.

The control process for implementing the medical waste treatment by my dry heat autoclave method, as illustrated in FIG. 4, begins with an initialization step 15, whereby an appropriate container of sharps and other medical waste is loaded into the chamber of unit 2 with the door mechanically latched and the operator setting an appropriate temperature set point and cycle time by way of keyboard entry means 6. In this regard, although ordinarily maintaining a temperature 320° for a period of two hours and twenty minutes should be sufficient to meet regulations for obtaining sterilized waste products, it is contemplated that the minimum set points to be included in the exemplary embodiment would be a temperature set point of about 350° F. in order to assure compliance with governmental regulations. As will be appreciated by the artisan, additional higher set points for both time and temperature may optionally be included for keyboard entry in order to provide for maximum loading of the heat chamber or to provide for materials having higher melting temperatures. All of the available temperature set point selections, however, should be well below the flash points of the waste material to be treated.

Subsequent to the initialization step 15 the operator would proceed to set the electrically operated solenoid lock as at 16, which, for example, may be implemented by way of a start key or button included in keyboard entry means 6 of FIG. 1. Setting of the electrical lock will additionally start the heating cycle, as at 17, wherein electrical energy is supplied to the heating elements of unit 2, as well as the afterburner unit in accordance with the temperature and time set points produced in the nonvolatile RAM memory as in step 15. During the heating cycle, clock pulses supplied by the microprocessor may be used to decrement the selected and stored time period data.

As to temperature control, in addition to storing the selected temperature set point in memory, a thermocouple of the nature taught in my U.S. Pat. No. 4,451,726 which issued on May 29, 1984 may be included in the heat chamber of unit 2 for accurately determining the chamber temperature. Processor 13 repetitively compares the sensed temperature with the temperature set point and reduces or maintains tile supply of electrical energy to the chamber heating elements so as to maintain the chamber at the selected desired temperature during the heating cycle.

Additionally, it may be desirable at the beginning of a heating cycle to raise the temperature in stages in a manner similar to that taught in my U.S. Pat. No. 4,367,399 which issued on Jan. 4, 1983. Such a staged increased in temperature would be desirable here since residual fluid may be contained in the hypodermic syringe, tubing or other waste products, which should be vaporized and driven off through the afterburner unit prior to melting and possible entrapment of the fluids within the plastic bodies.

After a sufficient time to drive off such residual fluids, which time can be included is the initially set time period, the temperature may be raised to the selected temperature set point which would be sufficient to melt the plastic bodies of the waste products. Presuming no interruption of the heating cycle occurs, such as might occur due to a power outage, the heating cycle proceeds at the selected temperature for the remainder of the time period set by the operator.

However, where a heating cycle has been interrupted, such an event would be detected at step 18 such as by the operation of a solenoid operated switch or other switching device connected to cause a flag bit in memory to be set indicating that an interruption has occurred. Upon reapplication of power, the flag bit would be sensed by processor 13 causing a reinstitution of the heating cycle from the beginning as graphically illustrated by the Y (Yes) response to the interrogation at step 18.

Again presuming no cycle interruption has occurred, the cycle will be maintained until completion, as sensed at step 19. Such cycle completion may be detected by the processor determining that the stored timing cycle data has been decremented to zero. As indicated at step 19 of FIG. 4, the CYCLE COMPLETE step is repetitively performed each time the time period data is reduced until no time is left. Upon detection of a completed heating cycle the microprocessor will de-energize the chamber heating units, as well as instituting step 20 wherein the chamber temperature is continually compared with a pre-stored temperature, such as room temperature, for determining when the heat generator unit 2 may be opened and the contents safely handled. Upon detection of the unit cooling down to the desired safe temperature, the microprocessor will apply electrical energy to the solenoid 12 to thus electrically release the latching mechanism, as at step 21, so that the door 3 may then be opened.

Although in the above noted process the afterburner unit may be de-energized along with the chamber heating units, it is believed that the more desirable procedure would be to de-energize the afterburner element at some later time when the heating chamber of unit 2 is at or near room temperature. The latter procedure would assure continued elimination of metallic contents and odors during the cooling off period, as well as during the heating cycle.

FIGS. 5A, 5B, 6, 7A and 7B are various views of two exemplary embodiments of containers useful for holding medical waste products before and during the above noted heat cycle. Prior to the heating cycle, the readily accessible openings of the containers allow the safe insertion and accumulation of waste products. During the heating cycle, a raised element in the container supports the waste products above the bottom of the container.

As previously noted, the temperatures in the disclosed dry heat generator during the heat cycle are held well below the flash points of the waste materials to be treated. However, the contemplated temperatures are sufficiently high to melt plastic bodies included in the waste products such that the molten material will flow through or over the sides of the raised element to the bottom of the container, thus separating the plastic and non-plastic materials.

Figure 5A:
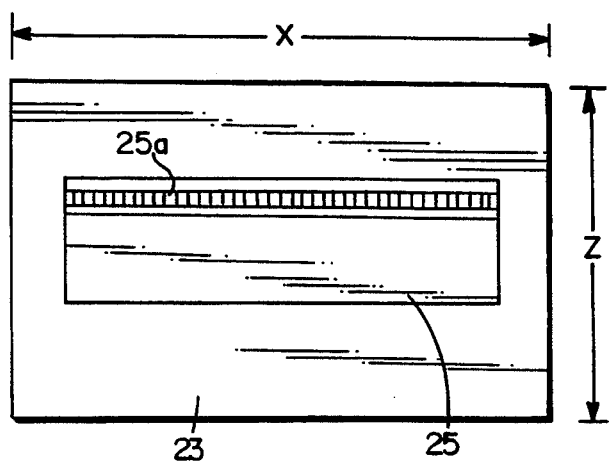
FIGS. 5A and 5B illustrate the top and side views, respectively, of an exemplary container holding medical waste products for use in the dry heat autoclave or generator of FIG. 1.
Figure 5B:
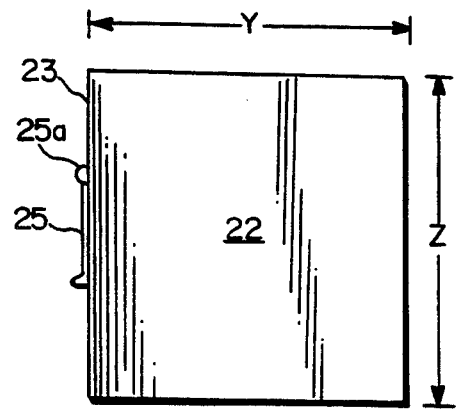
Figure 6:
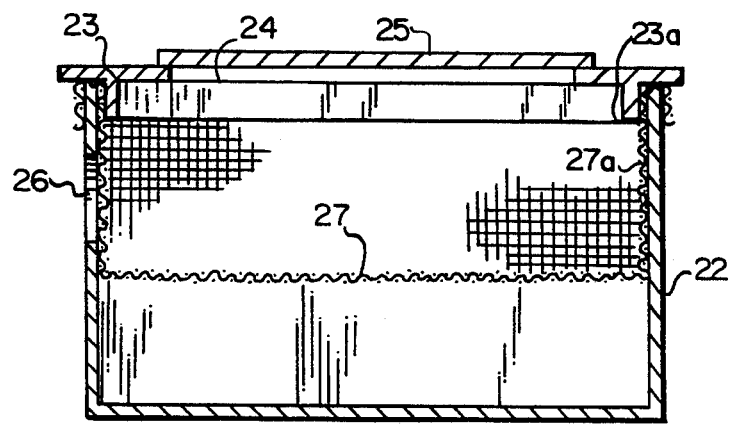
FIG. 6 illustrates a front cross sectional view of the container of FIGS. 5A and 5B illustrating a removable cover and a raised interior grid element of the container used for supporting and separating plastic and non-plastic waste elements during a heat cycle.

Turning to the embodiment of the container illustrated in FIGS. 5A, 5B and 6, the container 22 may be of a rectangular construction as viewed from the top as in FIG. 5A, as well as from the side as shown in FIG. 5B. The outside dimensions of the container are generally indicated as x, y and z, with exemplary dimensions for x, y and z of 8 inches, 6 inches and 4 inches, respectively. As will be appreciated, however, the dimensions will vary depending on the size and nature of the waste products. It is contemplated that the container 22 will be made of stainless steel, aluminum or other suitable leakproof materials capable of withstanding the above noted temperatures. Additionally, the top 23 of the container in the illustrated embodiment is removable and is held in place by a friction fit between the lower edge portion 23a of the cover and the inner dimensions of the side walls of the container. Still further, the container cover 23 includes an elongated opening 24 to permit the medical waste materials to be inserted into the container. It is further contemplated that the cover 23 will include a lid 25 which is hingeably attached at 25a to the top of the cover element 23 for covering the opening 24 when it is not in use. Moreover, the container preferably also includes a side opening 26 which will allow the insertion of medical waste products into the container by way of a side entrance, as well as the top opening 24.

As may be seen from the cross sectional view of the container, as shown in FIG. 6, included within the interior of the container 22 is a raised portion 27 which may be supported above the bottom of the container by leg portions (not shown) or suspended by portions 27a which are formed by extensions of portion 27 to extend in an upward direction along the container walls and bent over the top edges of the container. Other alternative means may be used to suspend element 27 at an appropriate height, such as a flange attached to the container which extends around the four walls.

It is contemplated that the raised portion 27, as well as the suspending portions 27a, may be made of metal wire grid or screen material, such as conventional hardware wire, wherein the size of the openings therein is sufficiently large to allow the molten plastic formed during the heat cycle to pass through the element to the bottom of the container. The size of the openings, however, should be sufficiently small as to prevent non-plastic waste elements, such as metal cannulas, rubber plungers and the like from passing through the screen, thus separating the plastic and non-plastic materials. That is to say, when the container 22 having medical waste products inserted therein is placed in the above noted dry heat generator and is subjected to a heat cycle, the non-plastic elements of the waste will be separated and remain suspended on the raised separator element 27; whereas, the molten plastic will flow through the separator and will collect in a molten pool at the bottom of the container. Subsequent to the heat cycle and cool down the container can be opened and the now sterile and separated plastic and non-plastic elements can be separately processed for subsequent recovery and recycling.

As previously noted, lid 25 which may be hinged at 25a through the use of a conventional piano type hinge and may be opened to expose opening 24 for the insertion of medical waste products. Additionally, since the extension members 27a may include openings sized and aligned with opening 26, the container side opening 26 may also be used for insertion of medical waste products into the container. Alternatively, side separator elements 27a may be constructed to extend in the downward direction to support horizontal portion 27 at an appropriate height. In either event flange portions 23a of the cover are sized and positioned so as to form a friction fit with the interior wall dimensions of the container 22. As will be appreciated by the artisan, other conventional means including solder, latching elements and the like may be used to attach cover 23 to the container 22 to prevent accidental separation and spillage of the contents prior to sterilization.

In this regard, it is desirable that container 22 and cover 23 are not easily separated when being handled during the insertion of medical wastes or in moving the container to the heat generator of FIG. 1 in order to prevent accidental spillage of the contaminated contents of the container. For example, it would be undesirable to have the cover 23 easily separate from the container even when the container is oriented with the opening 26 in an upright position for the insertion of medical waste products.

Figure 7A:
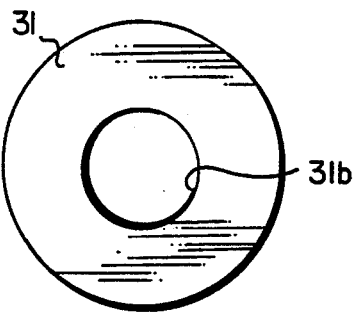
FIGS. 7A and 7B are a top view and side cross sectional view, respectively, of another exemplary container including a raised interior platform of sheet metal having a diameter slightly smaller than the inside diameter of the container.
Figure 7B:
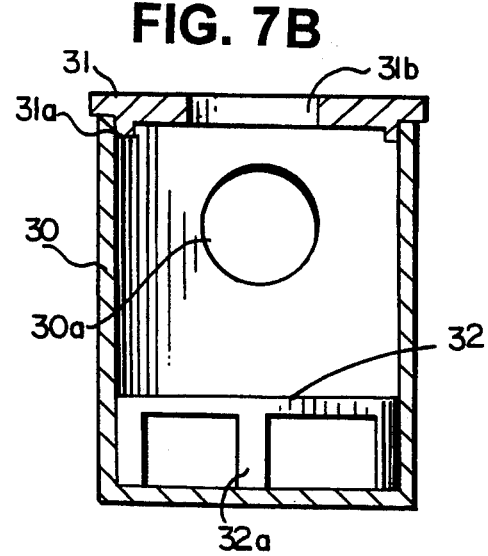

An alternative exemplary embodiment of a container useful in the herein disclosed method of sterilizing and separating plastic and non-plastic medical waste products is illustrated in FIGS. 7A and 7B. As may be seen from the drawings, the container 30 is of a circular cylindrical configuration and includes a side opening 30a for the insertion of medical waste products into the container. Additionally included is a cover 31 which, as illustrated, includes downwardly extending flange portion 31a for forming a friction fit with the interior wall of the container 30. As with the first embodiment illustrated in FIGS. 5A, 5B and 6, other conventional manners of attaching the cover 31 to the container may be used in order to prevent accidental spillage of contaminated waste products from the container.

As illustrated in FIGS. 7A and 7B, cover 31 also includes an opening 31b which may be conveniently used for the insertion of contaminated medical waste products. Container 30 further includes a raised insert portion 32 which is sized to be of slightly smaller diameter than the inner walls of the container so as to allow molten plastic to flow over the surface of insert 32 and down the side walls of the container to form a molten pool at the bottom of the container during a heat cycle. The difference in diameters of the insert and interior dimensions of the container should be sufficient to allow the free flow of the molten plastic but not sufficiently great as to allow non-plastic waste elements to pass to the bottom of the container.

Figure 8A:
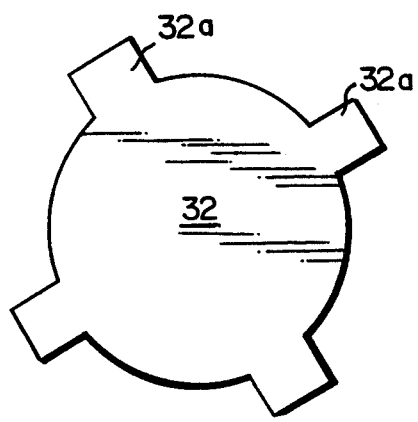
FIGS. 8A and 8B are a top view and a side view, respectively, of an exemplary raised platform element of FIG. 7B both before and after the leg portions are bent to the operative position of FIG. 7B.
Figure 8B:
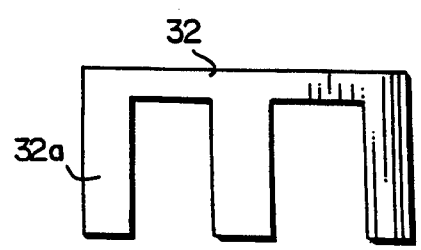

The raised insert 32 is constructed of sheet metal and is formed in the general manner illustrated in FIGS. 8A and 8B so as to include leg portions 32a. The leg portions are bent in a downwardly extending direction and are dimensioned to be sufficiently long as to position the top of the insert at a convenient workable height within the container. Leg portions 32a are bent in such a manner that the ends of the legs extend slightly in the outward direction so as to contact the interior wall surfaces of the container. Forming the leg portions in the above noted manner not only position the insert at a convenient height in the container (¾ inch, for example) but also tend to prevent the insert from turning over when being installed in the container.

Although the container 30 may be constructed so as to have any convenient dimensions depending on the nature and size of the waste products, exemplary such dimensions would include a 6 inch diameter container with a height of approximately 8 inches. Additionally, although the openings 30a and 31b may be of any convenient size, an exemplary size would be 1 17/16 inches so as to accept conventional metal plug closure means for each of the openings. Moreover, the materials contemplated for use in forming the container, cover and insert are the same as those exemplary materials specified for the container of FIGS. 5A and 5B.

The contemplated use of the container of FIGS. 7A and 7B is also similar to that of the first exemplary embodiment. That is to say, medical waste products comprising plastic and non-plastic elements are inserted into the container by way of the openings 30a and 31b such that they will rest on the top of the raised platform 32. When full or at the end of a workday, conventional metal plug elements may be used to close the openings to prevent accidental spillage in the handling of the container. Thereafter, the container is placed in the dry heat generator of FIGS. 1 and 9 where it is subjected to a heat cycle for the sterilization and separation of the container contents.

As previously noted, during the heat cycle the plastic contents will melt and overflow from the top of the insert element 32 down the interior sides of the container wall to form a molten pool in the bottom of the container; whereas, the non-plastic metal and/or rubber waste constituents will remain on top of the insert element and are thus separated from the plastic materials. In this regard, although the raised insert element 32 has been indicated to be constructed of sheet metal, vis-a-vis, the wire grid construction of insert element 27 of FIG. 6, for example, it will be appreciated by the artisan that insert element 32 may also be constructed of hardware wire as in the embodiment of FIG. 6. Moreover, the insert element of FIG. 6 may alternatively be constructed of sheet metal with leg elements bent in the downward direction but constructed in a rectangular configuration as opposed to the circular configuration of FIG. 8A, for example.

Figure 9:
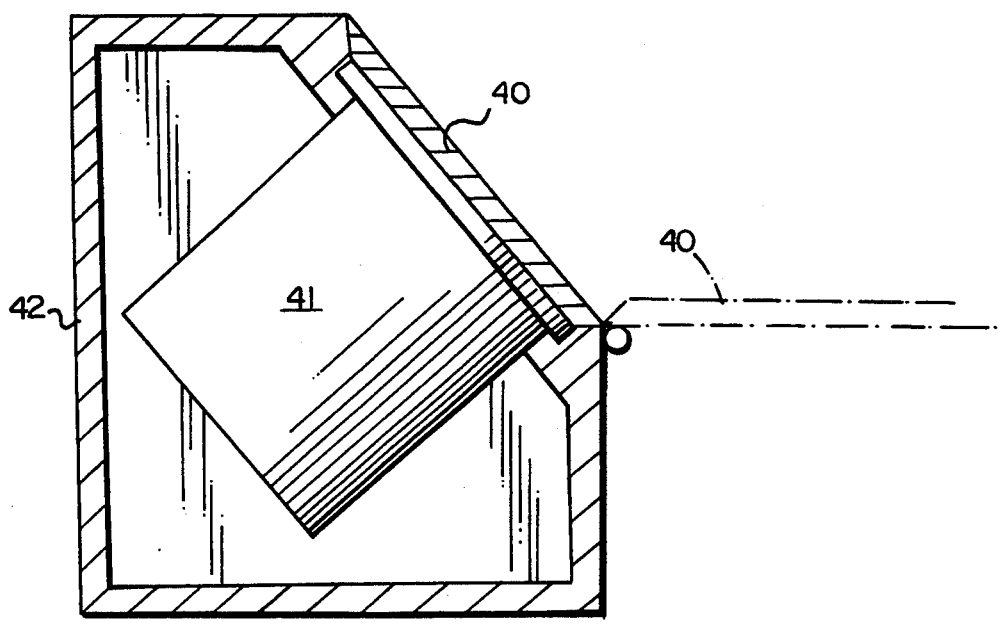
FIG. 9 is a side cross sectional view of an alternative front loading configuration of the dry heat generator of FIG. 1 with the door and the waste container mounted in angular positions.

As a still further alternative embodiment, the dry heat generator of FIG. 1 may be reconfigured in the general manner illustrated in FIG. 9 wherein the heat generator may include a hinged front opening door 40 inclined at approximately 45° The exterior wall portions 42 illustrated in cross section may be configured in the general manner illustrated in FIG. 9 so as to accept and partially support a container 41 which may, for example, be configured in the manner illustrated in FIG. 7B. Additional support for the container may be obtained by configuring the interior wall portions of the generator which would include heating elements and the like to include a recess of the general shape of the container 41.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. A method of heat treating and separating plastic and non-plastic elements of potentially infectious waste products, said method comprising the steps of:
   providing waste products comprising plastic and non-plastic elements:
   placing said waste products in a container having a bottom and side surfaces so that said products are positioned in a spaced relationship from the bottom of the container;
   placing said container in a dry heat generating chamber;
   heating said chamber, said container and its contents at a selectable temperature above tile melting point of said plastic elements but below tile flash points of said waste products; and
   maintaining said temperature for a period of time sufficient to sterilize said waste products and to convert said plastic elements to a molten state;
   allowing the molten plastic to flow to the container bottom to form a liquid plastic pool while maintaining said non-plastic elements in said spaced relationship from the bottom of the container,
   whereby said waste products are rendered sterile and said non-plastic elements are substantially separated from said plastic elements.

2. A method as in claim 1 further comprising the step of:
   cooling said container and its contents to a temperature whereby said liquid pool solidifies.

3. A method as in claim 2 further including the step of:
   removing the solidified liquid pool and non-plastic elements from said container for subsequent separate recycling processing.

4. A method as in claim 1 further including the step of:
   providing said dry heat generator with means for preventing access to said container and its contents until they have been heated at said selected temperature for said period of time.

5. A method as in claim 4 further comprising the step of:
   preventing access to said container and its contents after heating until they have cooled to substantially room temperature.

6. A method as in claim 1 further including the step of:
   constructing said container to include a platform element positioned to maintain said spaced relationship and constructed to allow the molten plastic to pass through or over said platform element.

7. A method as in claim 1 further comprising the step of:
   treating fumes from the heated container and its contents to substantially remove odors as well as vaporized metallic and particle contents.

8. A method as in claim 1 further comprising the step of:

treating fumes from the heated container and its contents to substantially remove odors as well as vaporized metallic and particle contents.

9. A heat generator apparatus for treating and separating plastic and non-plastic elements of potentially infectious waste products, said apparatus comprising:

a chamber including heating elements for heating said chamber to a selectable temperature;

input means for setting said selectable temperature and for setting a selectable time period for maintaining the selected temperature;

said selectable temperatures and time periods, in combination, being at least sufficient to sterilize waste products and melt plastic elements to a molten state, said selectable temperatures additionally being below the flash points of said waste products;

a container within said chamber for holding said waste products and having a bottom and side surfaces, said container including a platform device and means for holding said platform device and said waste products in a spaced relationship from the bottom of the container said platform device including means for allowing the molten plastic to flow to the container bottom while maintaining said non-plastic elements in said spaced relationship from the container bottom, whereby said waste products after heating at said selectable temperature for said selectable time period are rendered sterile and said non-plastic elements are substantially separated from said plastic elements.

10. An apparatus as in claim 9 wherein said means for allowing the molten plastic to flow is a metal wire screen material having openings sufficiently large to allow molten plastic to pass through the screen material.

11. An apparatus as in claim 9 wherein said contained includes a cover attached to said side surfaces of said container.

12. An apparatus as in claim 11 wherein said cover includes an opening for inserting waste products into said container.

13. An apparatus as in claim 12 wherein said cover includes a hinged lid for closing said opening.

14. An apparatus as in claim 9 further including an opening in said side surfaces for inserting waste products into said container.

15. An apparatus as in claim 14 further including metal plug means for closing said opening.

16. An apparatus as in claim 9 wherein said means for allowing the molten plastic to flow is formed of sheet metal having a continuous surface which is sized and positioned in the container so as to allow molten plastic to flow over said surface and down the side surface of said container to form a liquid plastic pool on the bottom of the container.

17. An apparatus as in claim 16 wherein said means for holding said platform device in said spaced relationship is integral with said sheet metal continuous surface.

18. An apparatus as in claim 9 wherein said chamber includes a top and at least one side wall and a hinged door mounted at an angle and connecting said top and said at least one side wall, said container being mounted and supported below said door by said top and said at least one side wall.

* * * * *